(12) United States Patent
Yan et al.

(10) Patent No.: US 6,183,725 B1
(45) Date of Patent: *Feb. 6, 2001

(54) GAS MIXTURES USEFUL AS ULTRASOUND CONTRAST MEDIA, CONTRAST AGENTS CONTAINING THE MEDIA AND METHOD

(75) Inventors: Feng Yan, Carouge; Michel Schneider, Troinex, both of (CH)

(73) Assignee: Bracco Research S.A., Carouge (CH)

( * ) Notice: Under 35 U.S.C. 154(b), the term of this patent shall be extended for 0 days.

This patent is subject to a terminal disclaimer.

(21) Appl. No.: 09/021,367

(22) Filed: Feb. 10, 1998

Related U.S. Application Data

(62) Division of application No. 08/848,912, filed on May 1, 1997, now Pat. No. 5,846,518, which is a division of application No. 08/637,346, filed on Apr. 25, 1996, which is a division of application No. 08/352,108, filed on Nov. 30, 1994, now Pat. No. 5,556,610, which is a division of application No. 07/991,237, filed on Dec. 16, 1992, now Pat. No. 5,413,774.

(30) Foreign Application Priority Data

Dec. 15, 1993 (EP) .................................................. 93810885

(51) Int. Cl.$^7$ ....................................................... A61B 8/13
(52) U.S. Cl. .......................................... 424/9.51; 424/9.52
(58) Field of Search ................................. 424/9.52, 9.51; 600/458

(56) References Cited

U.S. PATENT DOCUMENTS

| 4,224,179 | 9/1980 | Schneider ............................... 264/4.6 |
| 4,229,360 | 10/1980 | Schneider et al. .................... 264/4.6 |

(List continued on next page.)

FOREIGN PATENT DOCUMENTS

| 40651/89 | 3/1990 | (AU) . |
| 70982/91 | 10/1991 | (AU) . |

(List continued on next page.)

OTHER PUBLICATIONS deJong et al Ultrasonics 1992 vol. 30 No. 2 pp. 95–103 Absorption and scatter of encapsulated gas etc.

(List continued on next page.)

*Primary Examiner*—Gary E. Hollinden
(74) *Attorney, Agent, or Firm*—Nixon & Vanderhye

(57) ABSTRACT

The invention relates to injectable media for ultrasonic echography in the form of microbubbles or microballoons comprising at least two biocompatible substances A and B (gaseous at the body temperature) forming a mixture which when in suspension with usual surfactants, additives and stabilisers provides useful ultrasound contrast agents. At least one of the components (B) in the mixture is a gas whose molecular weight is greater than 80 daltons and whose solubility in water is below 0.0283 ml per ml of water at standard conditions. The presence of the first component (B) in the contrast medium may vary between 0.5 and 41 volume percent. The other component (A) of the ultrasound contrast media is a gas or a mixture of gases whose molecular weight is below 80 daltons. The second component is present in a proportion of between 59–99.5% by vol., and is preferably chosen from oxygen, air, nitrogen, carbon dioxide or mixtures thereof. Gas mixtures described are found to be very effective as ultrasound contrast media. The invention also comprises a method of making the ultrasound contrast medium, the contrast agent and the ultrasound agent kit.

29 Claims, 6 Drawing Sheets

U.S. PATENT DOCUMENTS

| | | | |
|---|---|---|---|
| 4,256,251 | 3/1981 | Moshofsky | 227/120 |
| 4,265,251 * | 5/1981 | Tickner | 128/660 |
| 4,276,885 | 7/1981 | Tickner et al. | 424/9.52 |
| 4,316,391 | 2/1982 | Tickner | 73/861.25 |
| 4,442,843 | 4/1984 | Rasor et al. | 424/9.52 |
| 4,466,442 | 8/1984 | Hilmann et al. | 600/431 |
| 4,544,545 | 10/1985 | Ryan et al. | 424/1.21 |
| 4,572,203 | 2/1986 | Feinstein | 424/9.52 |
| 4,657,756 | 4/1987 | Rasor et al. | 424/9.52 |
| 4,681,119 | 7/1987 | Rasor et al. | 424/9.52 |
| 4,684,479 | 8/1987 | D'Arrigo | 252/307 |
| 4,718,433 | 1/1988 | Feinstein | 424/9.52 |
| 4,774,958 | 10/1988 | Feinstein | 424/9.52 |
| 4,832,941 | 5/1989 | Berwing et al. | 424/9.52 |
| 4,844,882 | 7/1989 | Widder et al. | 424/9.52 |
| 4,859,363 | 8/1989 | Davis et al. | 516/76 |
| 4,900,540 | 2/1990 | Ryan et al. | 424/9.51 |
| 4,957,656 | 9/1990 | Cerny et al. | 252/311 |
| 5,088,499 | 2/1992 | Unger | 424/9.51 |
| 5,123,414 | 6/1992 | Unger | 600/431 |
| 5,137,928 | 8/1992 | Erbel et al. | 521/56 |
| 5,141,738 | 8/1992 | Rasor et al. | 424/9.52 |
| 5,147,631 | 9/1992 | Glajch et al. | 424/9.52 |
| 5,310,540 * | 5/1994 | Giddey et al. | 424/9 |
| 5,380,519 * | 1/1995 | Schneider et al. | 424/9 |
| 5,425,366 | 6/1995 | Reinhardt et al. | 600/458 |
| 5,501,863 | 3/1996 | Rossling et al. | 424/489 |
| 5,556,610 | 9/1996 | Yan et al. | 424/9.52 |
| 5,558,854 * | 9/1996 | Quay | 424/9.52 |
| 5,558,856 * | 9/1996 | Klaveness et al. | 424/9.37 |
| 5,562,893 * | 10/1996 | Lohrmann | 424/9.52 |
| 5,599,523 | 2/1997 | Beller et al. | 424/9.52 |
| 5,639,443 * | 6/1997 | Schutt et al. | 424/9.52 |
| 5,711,933 | 1/1998 | Bichon et al. | 424/9.52 |

FOREIGN PATENT DOCUMENTS

| | | |
|---|---|---|
| 1232837 | 2/1988 | (CA) . |
| 1239092 | 7/1988 | (CA) . |
| 41 27 442 A1 | 2/1993 | (DE) . |
| 0 077 752 | 4/1983 | (EP) . |
| 0122624 | 10/1984 | (EP) . |
| 0131540 | 10/1985 | (EP) . |
| 0 245 019 | 11/1987 | (EP) . |
| 0 324 938 | 7/1989 | (EP) . |
| 0327490 | 8/1989 | (EP) . |
| 0441468 | 2/1990 | (EP) . |
| 0357163 | 3/1990 | (EP) . |
| 0 467 031 A2 | 1/1992 | (EP) . |
| 0494615 | 7/1992 | (EP) . |
| 0 554 213 A1 | 8/1993 | (EP) . |
| 0554213 * | 8/1993 | (EP) . |
| 0123235 | 10/1994 | (EP) . |
| WO 80/02365 | 11/1980 | (WO) . |
| WO 89/06978 | 8/1989 | (WO) . |
| WO 89/10118 | 11/1989 | (WO) . |
| WO 90/01952 | 3/1990 | (WO) . |
| WO91/12823 | 9/1991 | (WO) . |
| WO 91/15244 | 10/1991 | (WO) . |
| WO 92/11873 | 7/1992 | (WO) . |
| WO 92/17212 | 10/1992 | (WO) . |
| WO 92/17213 | 10/1992 | (WO) . |
| WO92/18164 | 10/1992 | (WO) . |
| WO 92/21382 | 12/1992 | (WO) . |
| WO 92/22247 | 12/1992 | (WO) . |
| WO 93/05819 | 4/1993 | (WO) . |
| WO 93/06869 | 4/1993 | (WO) . |
| WO93/05819 | 4/1993 | (WO) . |
| WO 93/17718 | 9/1993 | (WO) . |
| WO 94/16739 | 8/1994 | (WO) . |
| 84/2800 | 4/1984 | (ZA) . |

OTHER PUBLICATIONS deJong et al Ultrasonics 1991 vol. 29 Jul. pp. 324–330 Principles and recent developments in ultrasound etc.

Bleeker et al 1990 J. Ultrasound Med 9:461–471, 1990 pp. 462–471 On the Application of Ultrsonic Contrast etc.

Feinstein et al JACC vol. 16, No. 2 Aug. 1990: 316–24 Safety and Efficacy of a New Transpulmonary Ultrasound etc.

Amer Hearts Assn Monograph Circulation Part II vol. 72 No. 4 Oct. 1985 Abstracts of the $58^{th}$ Scientific Sessions.

Bleeker et al J. Acoust. Soc. Am. 87 (4) Apr. 1990 pp. 1792–1797 Ultrasonic characterization of Albunex® etc.

Epstein et al J. Chem. Physics vol. 18, No. 11, Nov. 1950 On the Stability of Gas Bubbles in Liquid–Gas Solutions.

Meltzer et al Ultrasound in Med & Biol vol. 7, No. 4 pp. 377–384 1981 Transmission of Ultrasonic Contrast etc.

Violante et al Investigative Radiology vol. 26 Nov. Supp 1991 Particle–Stabilized Bubbles for Enhanced etc.

Ohta et al Jpn J Med Ultrasonics vol. 18 No. 4 (1991) Effect of the Contrast Agent and the Agitation Method etc.

Feinstein et al Am J of Physiologic Imaging 1:12–18 (1986) Myocardial Contrast Echocardiography etc.

Widder et al AJR:147, Aug. 1986 Microbubbles as a Contrast Agent for Neurosonography and Ultrasound–etc.

Schlief Current Opinion in Radiology 1991, 3:198–207 Ultrasound Contrast Agents.

Fobbe et al Furtschr Rontgenstr 154.3 (1991)242–245 Farbkodierte Duplexsonographic und Ultra–etc.

Ophir et al Ultrasound in Med & Biol vol. 15 No. 4 pp. 319–333 1989 Contrast Agents in Diagnostic Ultrasound.

Swanson, pp. 682–687 "Chapter 22: Enhancement Agents for Ultrasound: Fundamentals" in Pharmaceuticals in Medical Imaging, (EDS. Swanson et al., MacMillan Publishing Company, New York, 1990).

Lincoff et al Intravitreal Longevity of Three Perfluorocarbon Gases, *Arch. Ophthalmology*, 98: 1610–1611 (1980).

Lincoff et al Intravitreal Expansion of Perfluorocarbon Bubbles, *Arch. Ophthalmology*, 98: 1646 (1980).

Lincoff et al The Perfluorocarbon Gases in the Treatment of Retinal Detachment, *Ophthalmology*, 90(5):546–551 (1983).

Lincoff et al Perfluoro–n–butane: A Gas for Maximum Duration Retinal Tamponade, *Arch Ophthalmology*, 101:460–463(1983).

Gardner et al (1988) "A Survey of Intraocular Gas Use in North America," *Arch Ophthalmol.* 106:1188–1189.

* cited by examiner

GAS MIXTURES USEFUL AS ULTRASOUND CONTRAST MEDIA, CONTRAST AGENTS CONTAINING THE MEDIA AND METHOD

This is a Rule 53(b) of application Ser. No. 08/848,912, filed May 1, 1997, now Pat. No. 5,846,518 which is a Divisional of application Ser. No. 08/637,346, filed Apr. 25, 1996, which is a divisional of Ser. No. 08/352,108, filed Nov. 30, 1994, now U.S. Pat. No. 5,556,610, which is a continuation-in-part of Ser. No. 07/991,237, filed Dec. 16, 1992, now U.S. Pat. No. 5,413,774.

TECHNICAL FIELD

The invention relates to contrast media for ultrasonic echography and injectable ultrasound contrast agents comprising dispersions of microparticles (microbubbles, microballoons or microcapsules) carrying the contrast media. In addition to microparticles the contrast agents comprise a physiologically acceptable aqueous carrier liquids which includes surfactants, additives and stabilisers. The invention also concerns methods of making the ultrasound contrast media and contrast agents and methods of using the same.

BACKGROUND ART

Recognition of the utility of injectable suspensions of gas microparticles as useful ultrasound contrast agents for diagnostic purposes has triggered considerable research and development towards improved dispersions of gas filled microballoons or microbubbles with higher stability, better resistance to pressure variations, good echogenicity, ease of manufacture, field use and storage. Many proposals for ultrasound contrast agents with such suspensions have been made. For example, aqueous suspensions usable as imaging agents in ultrasonic echography are disclosed in WO-A-91/15244 (Schneider et. al.), WO-A-92/11873 (Belier et. al.) or EP-A-0 077 752 (Schering).

WO-A-91/15244 (Schneider et. al.) discloses microbubble suspensions containing film forming surfactants in laminar and/or lamellar form and, optionally, hydrophilic stabilizers. The suspensions are obtained by exposing the laminarized surfactants to air or a gas prior to or after admixing with an aqueous phase. Conversion of film forming surfactants into lamellar form is carried out according to various techniques including high pressure homogenisation or sonication under acoustic or ultrasonic frequencies. The reported concentration of the microbubbles in these suspensions is between $10^8$ and $10^9$ bubbles/ml. The suspensions disclosed exhibit a fairly high stability during storage.

In WO-A-94/09829 (Schneider et. al.) it is shown that concentrations of the laminar and/or lamellar phospholipids used in the preparations of very stable aqueous suspensions may be as low as to correspond to a single monomolecular layer of the phospholipid around the microbubbles in the suspension. Stable, low phospholipid content (down to a few $\mu$g/ml) suspensions have been stored for prolonged periods without significant loss of microbubble count or echogenicity.

A method of imparting stability against pressure variations to suspensions of microbubbles or microballoons used as ultrasound contrast agents is disclosed in EP-A-0 554 213 (Schneider et al.). There, it has been shown that a significant enhancement of the stability of the microbubbles against collapse due to pressure variations upon injection may be achieved if commonly used air, nitrogen or other soluble gases are at least partially replaced by gases whose solubility in water expressed in litres of gas by litre of water under standard conditions divided by the square root of the molecular weight in daltons does not exceed 0.003. Gases disclosed which satisfy the above criteria are for example, $SeF_6$, $SF_6$, $CF_4$, $C_2F_6$, $C_2F_8$, $C_4F_{10}$, etc. These gases have been found to produce long lasting and ill vito verv stable microballoons which in turn provide high quality echographic images.

WO-A-92/17212 and WO-A-92/17213 (Klaveness et al.) disclose ultrasound contrast agents comprising microballoons having an envelope made of non-proteinaceous crosslinked or polymerised amphiphilic substances (e.g. phospholipids) and crosslinked proteins (e.g. albumin). Microballoons are encapsulating gases such as air, oxygen, hydrogen, nitrogen, helium, argon, $CH_4$, $SF_6$ or gas precursors such as sodium or ammonium bicarbonate.

WO-A-93/06869 (Mallinckrodt Medical Inc.) discloses a method of ultrasound imaging of a warm blooded animal in which a pharmaceutically acceptable gas or a mixture of gases is administered to the animal and the animal is scanned with an ultrasound probe. The gases or gas mixtures are administered by inhalation as apparently upon inhalation of the mixture for a few minutes, microbubbles will form in the blood stream of a warm blooded animals and the echographic image of tissue will change. The gases and gas mixtures disclosed include oxygen, nitrous oxide, $C_2H_6$, $SF_6$, xenon, perfluorocarbons, etc. Useful gases and gas mixtures are those which tend to form larger bubbles in the blood and may be typified by xenon and nitrous oxide and other weakly active general anesthetics such as sulfur hexafluoride. Illustrated mixtures contain either 20% of oxygen, 60–80% of sulfur hexafluoride, and/or 20% of nitrogen, xenon, nitrous oxide or ethylene or 20% of oxygen, 20% of nitrogen and 60% of xenon or nitrous oxide. The method is based on comparison of ultrasonic signals obtained during two different scans. The first, prior to inhalation of the gas mixture and the second, some time after inhalation.

An interesting concept has been disclosed in WO-A-93/05819 (Quay). The document discloses emulsions of liquid dodecafluoropentane or decafluorobutane and sorbitol in water which upon injection form gaseous microbubbles which resist pressure variations and provide a good echogenic signal. The substances in the emulsions, although liquid at ambient temperature, are highly volatile and easily vaporize at body temperature and form gaseous dispersions in a carrier liquid containing additives and stabilisers such as sorbitol. Upon injection, the droplets of the highly volatile substance rapidly disaggregate and generate a fair amount of very persistent microbubbles. The microbubbles which only contain the chosen substance e.g. dodecafluoropentane in pure form at exclusion of air or any other gas are stabilised by stabilising agents, e.g. sorbitol, Tween® 20 and soybean oil which are present in the emulsion carrier liquid. By generalisation, Quay found that the foregoing technique was applicable to a number of other non-liquid (gaseous) chemical substances which were brought into use via a criteria defined as a relationship between volume density, solubility and diffusivity (coefficient Q). The document claims that any biocompatible gas whose coefficient Q is greater than 5 is potentially useful as an echographic agent, and a list of about 180 gases/liquids which satisfy the criteria is presented. It follows from the document that to achieve the desired properties, contrast agents are to be made with substances whose coefficient Q must be greater than 5. The criteria defined is $Q = 4.0 \times 10^{-7} \times \rho / C_s D$ where $\rho$ is density of the gas, D is diffusivity of the gas in solution and $C_s$ is the water solubility of the gas, and this has been developed using a simple model in which diffusivities and solubilities of gases in water are used as the approximation closest to reality. Contrast agents obtained from pure i.e. non-admixed, substances chosen according to the above criteria have shown encouraging results. Tested on experimental dogs, the contrast agents have been reported to furnish promising results in the echography of the myocardium after peripheral venous injections (see Beppu S. et al. in Proceedings from 66th Scientific Session of the American Heart Association, Atlanta, October 1993). Depending on the dose, injections of 2.2% emulsion of dodecafluoropentane have been found to provide a mean opacification during up to 85 minutes. However, with doses at which opacification of the left heart was homogeneous, there was observed a decrease in oxygen saturation of arterial blood and an increase of pulmonic arterial systolic pressure were observed.

Many of the prior art compositions have merit and many are under intensive clinical tests. Many are at various stages of development. From various reports it however appears that, to date, only a very small number of contrast agents is capable of exploiting the full range of diagnostic possibilities basically provided by ultrasound echography. Indeed, only a few contrast agents are really useful and help the medical profession to profit from the diagnostic technique which, otherwise, represents one of the best non-invasive methods for analysing organs in the human body. Not many agents allow exploitation of the full potential of the ultrasound concept and this hampers wider use of the technique and/or of the imaging agents. Experimentation with the known echographic agents has shown that some provide insufficient backscatter to ensure good intensity and contrast or provide useful images only in certain percentage of the population which limits their utility as a diagnostic tool of general use. Others, because of poor resistance to pressure variations, are too short lived to allow meaningful measurements or useful images. Typically, contrast agents whose microbubbles or microballoons are filled with gases of high solubility in water poorly resist pressure variations. Suspensions of microballoons whose envelope is made from rigid materials are also ineffective as they do not resonate sufficiently in response to the acoustic waves. Noteworthy contrast agents which have a high resistance to pressure variations are those using gases with low solubilities in the aqueous carrier. The direct consequence of low solubility is low rate of resorption and slow elimination from the body. Imaging agents made from such very insoluble gases remain in the blood circulation for prolonged periods causing relapse or recirculation of the gas microbubbles which causes interference with images produced during the initial stages of the test. Such contrast agents are generally useful for imaging the left heart but because of slow resorption or elimination, they cannot be used effectively for perfusion measurements. Perfusion measurements are usually carried out by integration of the echographic response curve, this being a typically Gaussian function, appearing after a "single pass" of the imaging agent. Relapse or recirculation after the "single pass" is therefore undesirable, as the repetition would superpose and impair the final result. It is therefore generally admitted that the persistence over a certain period of the microbubbles or microballoons endowed with high pressure resistance is more disturbing than helpful. Echographic contrast agents with very persistent microbubbles are useful only for certain studies, e.g. vascular Doppler investigations. Agents used for imaging of the left heart and myocardium should provide clear images and should have good resistance to pressure variation but should not be overlasting and should not disturb images created immediately upon injection. Recirculation is not a desirable feature of agents whose intended use is to cover a range of applications and clear imaging. Obviously, it is highly desirable to modulate the pressure resistance or persistence of the contrast agent after injection, i.e. to use suspensions of bubbles (or microballoons) designed with sufficient pressure resistance but with controlled lire-time in the circulation. This demand is fulfilled by the invention below.

SUMMARY OF THE INVENTION

Briefly summarised, the invention relates to an injectable ultrasound contrast medium in the form of microbubbles or microballoons comprising at least two biocompatible, at the body temperature gaseous, substances A and B forming a mixture which when in suspension with usual surfactants, additives and stabilisers provides useful ultrasound contrast agents. At least one of the components (B) in the mixture is a gas whose molecular weight is above 80 daltons and whose solubility in water is below 0.0283 ml of gas per ml of water under standard conditions. Through out this document gas solubilities referred to correspond to the Bunsen coefficients and the molecular weights above 80 daltons are considered as relatively high, while the molecular weights below 80 daltons are considered as relatively low. The mixtures of the invention therefore may be defined as mixtures of in which the major portion of the mixture is comprised of "a relatively low" molecular weight gas or gases, while the minor portion of the mixture is comprised of "a relatively high" molecular weight gas or gas mixture. The quantity of this "minor" or activating component (B) in the contrast medium is practically always between 0.5 and 41 volume percent. The other component (A) of the ultrasound contrast media may be a gas or a mixture of gases whose solubility in water is above that of nitrogen (0.0144 ml/ml of water under standard conditions) and whose quantity in the mixture is practically always in a proportion of between 59–99.5% by vol. This "major" or dominating component is preferably a gas or gases whose molecular weights are relatively low, usually below 80 daltons, and is chosen from gases such as oxygen, air, nitrogen, carbon dioxide or mixtures thereof.

In the ultrasound contrast medium of the invention the gas whose molecular weight is above 80 daltons may be a mixture of gases or mixture of substances which are gaseous at body temperature but which, at ambient temperatures, may be in the liquid state. Such gaseous or liquid substances may be useful in the contrast media of the invention as long as the molecular weight of each such substance is greater than 80 daltons and the solubility in water of each substance is below 0.0283 ml of gas per ml of water under standard conditions.

When filled with the contrast media of the invention and dispersed in an aqueous carrier containing usual surfactants, additives and stabilisers, the microbubbles formed provide an injectable contrast agent for ultrasonic imaging, of controlled resistance to pressure variations and modulated persistence after injection. In addition to the microbubbles, the contrast agent of the invention will contain surfactants stabilising the microbubble evanescent gas/liquid envelope, and optionally, hydrophilic agents and other additives. The additives may include block copolymers of polyoxypropylene and polyoxyethylene (poloxamers), polyoxyethylene-sorbitans, sorbitol, glycerol-polyalkylene stearate, glycerolpolyoxyethylene ricinoleate, homo- and copolymers of polyalkylene glycols, soybean-oil as well as hydrogenated derivatives, ethers and esters of sucrose or other carbohydrates with fatty acids, fatty alcohols, glycerides of soya-oil, dextran, sucrose and carbohydrates. Surfactants may be film forming and non-film forming and may include polymerizable amphiphilic compounds of the type of linoleyl-lecithins or polyethylene dodecanoate. Preferably, the surfactants comprise one or more film forming surfactants in lamellar or laminar form selected between phosphatidic acid, phosphatidylcholine, phosphatidylethanolamine, phosphatidylserine, phosphatidylglycerol, phosphatidylinositol, cardiolipin, sphingomyelin and mixtures thereof.

The invention also comprises a method of making the ultrasound contrast agents by suspending in a physiologically acceptable carrier containing usual surfactants and stabilisers, gas filled microbubbles or microballoons comprising a mixture of gases at least one of which is a gas whose minimum effective amount in the mixture may be determined according to the expression:

$$B_c\% = K/e^{b\ M_{wt}} + C$$

in which $B_c\%$ (by vol.) is the total quantity of the component B in the mixture, K, C & b are constants with values of 140, −10.8 and 0.012 respectively, $M_{wt}$ represents the molecular weight of the component B exceeding 80. The contrast agents made according to the present method comprise suspensions of microbubbles or microballoons with excellent resistance to pressure variations and a controlled resorption rate.

The invention also includes a kit comprising a dry formulation which is usually stored under a mixture of gases and/or liquids that are converted into gases at body temperature. When dispersed in a physiologically acceptable carrier liquid, the dry formulation with the mixture of gases and/or liquids produces the ultrasound contrast agent of the invention. A method of storage of the dry lyophilised formulation in the presence of the ultrasound contrast media is also disclosed.

The invention further comprises a method of making contrast agents with microbubbles containing the ultrasound contrast media, as well as their use in imaging of organs in human or animal body.

DETAILED DESCRIPTION OF THE INVENTION

Figure 1:
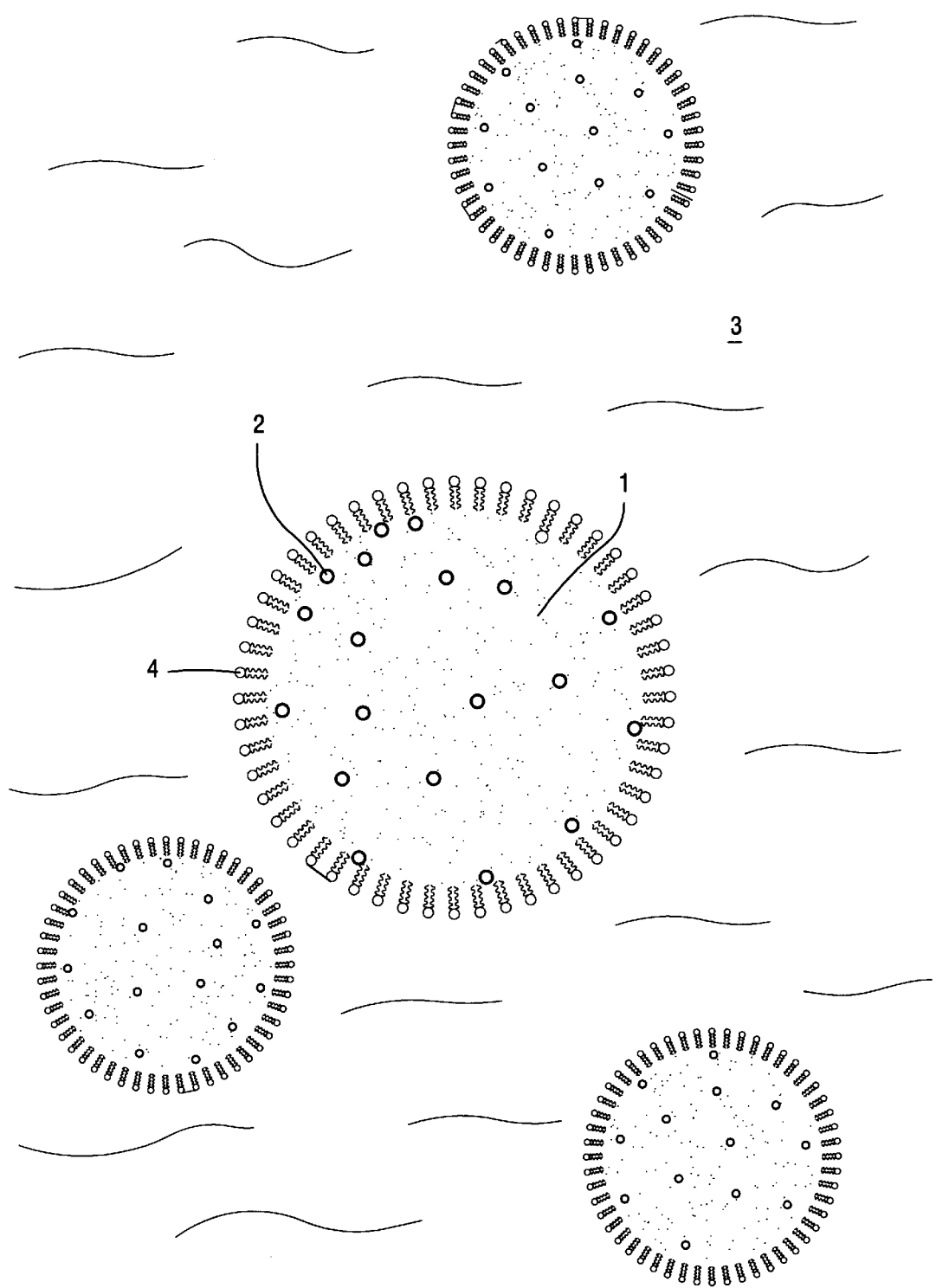
FIG. 1 is a schematic presentation of an ultrasound contrast medium according to the invention.

This invention is based on the unexpected finding that an ultrasound contrast medium comprising bubbles filled with a mixture of at least two biocompatible gaseous or at body temperature gaseous substances A (major or a relatively low molecular weight) and B (activating or a relatively high molecular weight), will provide, in suspension with usual surfactants, additives and stabilisers, injectable ultrasound contrast agents that combine desirable resistance to pressure and a shorter life time in the circulation, both of these parameters being controllable at will. As long as at least one of the (activating) substances or components in the mixture with molecular weight greater than 80 daltons (relatively high molecular weight) is present in certain minimal proportion and as long as its solubility in water is below 0.0283 ml of gas per ml of water at standard conditions, the ultrasound contrast medium will provide echographic properties as good as that obtained when using the pure substances alone. By "activating" it is meant the substance or component which imparts its physical properties to the other components in the mixture rendering the mixture, in terms of echogenicity and resistance to pressure variations, behave the same or almost the same as the substance or component alone (in pure form). The quantity of the first, activating or high molecular weight, component in the contrast medium in most cases vary from as low as 0.5 volume percent (for substances with high molecular weight and low solubility in water) to 41 volume percent. The experiments have shown that substances with the molecular weight below 80 daltons ("low molecular weight") are not suitable as the activating componets and that the upper limit of the molecular weight is difficult to establish as all compounds tested were effective as long as their molecular weight was relatively high i.e. above 80. Thus compounds with the molecular weight of about 240 daltons such as decafluorobutane or 290 daltons such as perfluoropentane have been found as effective activating component. Also there are indications that substances such as 1,2,3-nonadecane tricarboxylic acid, 2-hydroxy-trimethylester with the molecular weight sightly over 500 daltons may also be used as an activating, high molecular weight, component. The other "major" component is correspondingly present in an amount of 59 to 99.5% by volume and may be a gas or gases whose solubility in water is greater than that of nitrogen (0.0144 ml/ml of water under standard conditions). The second component is preferably oxygen, air, nitrogen, carbon dioxide or mixtures thereof and more preferably oxygen or air. However, for the component A, other less common gases like argon, xenon, krypton, $CHClF_2$ or nitrous oxide may also be used. Some of these less common gases may have molecular weights higher than that of $O_2$, $N_2$, air, $CO_2$, etc., for instance above 80 daltons but, in this case, their solubility in water will exceed that of the gases of cathegory B i.e. will be above 0.0283 ml/ml of water.

It was quite unexpected to find that suspending in an aqueous carrier a mixture formed of as little as 0.5% by volume of a substance such as dodecafluoropentane, or 0.8% by volume of decafluorobutane in admixture with air will produce microbubbles giving excellent echographic images in vivo and resistance to pressure variations. This is particularly surprising since it was heretofore considered necessary that in order to obtain good echographic images of the left heart and the myocardium, these substances, and for that matter a number of others, be used at 100% concentrations, i.e. in pure form (without air). Experiments with mixtures containing different mounts of these, low water solubility, substances and air have shown that he echographic images are as good as those obtained under similar conditions using echographic agents made with only pure substances. Early studies have shown that rapid elimination of air microbubbles in he circulation takes place because this otherwise physiologically preferred as is quickly resorbed by dilution and that evanescence of the microbubbles may be reduced through the use of various surfactants, additives and stabilisers. In the early days of development, as a cure to the evanescence problem, microballoons or microvesicles with a material wall have also been proposed. Microvesicles with walls made from natural or synthetic polymers such as lipid bilayers (liposomes) or denaturated proteins like albumin filled with air or $CO_2$ have been proposed. The poor resistance to pressure variations and the consequent loss of echogenicity of the older contrast agents has inspired a search for gaseous particles with greater resistance to the pressure variations occuring in the blood stream. Hence, filler gases such as sulfur hexafluoride of more recently dodecafluoropentane have been proposed. Experimentation with these gases have indicated that upon injection, the suspensions of microbubbles made with these gases taken alone are indeed very resistant to collapse in the blood circulation. As a result of these initial findings, close to 200 different gases have been identified as potentially useful for making ultrasound contrast agents. It has thus been unexpectedly found that by mixing oxygen or air with some of these gases resistant to pressure one may obtain ultrasound agents which will have physiologically better tolerance and/or shorter resorption half-life than pure sulfur hexafluoride or dodecafluoropentane, still retaining the good pressure resistance of these gases when taken alone. It is postulated that such surprising behaviour of the ultrasound medium of the invention comes from the fact that in the microbubbles containing the gas mixtures diffusion of air into surrounding liquid is slowed by the presence of the large molecules of gas or gases whose solubilities in water are about the same or lower than that of air or oxygen. Although the reasons for this surprising behaviour are yet unexplained, it can be postulated that the molecules of the high molecular weight gas, even though in very minor amount, do actually "plug the holes" in the microbubbles boundary and thus prevent escape of the low molecular weight gas by transmembrane diffusion. A graphical presentation of this model is shown in the FIG. 1 where the microbubble containing air (1) admixed with a gas whose molecular weight is above 30 daltons (2) is suspended in an aqueous medium (3). The evanescent outer layer (4) stabilised by a surfactant (e.g. phospholipid) keeps the gas mixture within contained volume defining the microbubble. The activating or minority gas B being uniformly dispersed through out the microbubble volume will have a slower diffusion and ultimatelly will block the pores of, in the aqueous solution spontaneously formed surfactant membrane-like envelope, thus preventing rapid departure of the smaller and typically more soluble majority component A. On the other hand, the activating or minor component gas (B) exhibit greater affinity for the lipophilic part of the surfactant used for stabilisation of the evanescent envelope than oxygen or air. Thus according to another hypothesis these gases tend to concentrate in the vicinity of the membrane preventing or slowing diffusion of the smaller gas(es) across the membrane. Be that as it may, the experimental data gathered suggest that for preparation of echographic media of the invention, the required amount of the activating gas in the mixture is that which corresponds to blocking the porosity of the given membrane material or to the amount required for a monomolecular layer formed on the inner wall of the microbubbles. Therefore, the minimum amount required is that which is needed to block the pores or cover the inner wall of the membrane to prevent escape and resorption of the low molecular weight component. It is also believed that the superior properties of the ultrasound contrast medium of the invention comes form the combined use of nitrogen, carbon dioxide, oxygen or air (essentially an oxygen/nitrogen mixture) with other gases. Functionally, these biologically and physiologically compatible gases provide important characteristics of the media in question thus ensuring their advantageous properties. Although, the ultrasound contrast media of the invention may be made with a number of other gases serving as the majority or component A, oxygen and air are preferred. In the context of this document air is treated as a "one component" gas.

According to the invention, ultrasound contrast media with high resistance to pressure variations combined with relatively rapid resorption, i.e. clearance in the body can be obtained when using a gas or gases whose molecular weights is/are above 80 daltons in admixture with gas or gases whose solubilites in water are greater than 0.0144 ml/ml of water and molecular weight(s) is/are usually below 80 daltons. Gases such as oxygen or air mixed with substances which are gases at the body temperature but which at the ambient temperatures may be in the liquid state will produce echographic media that will possess all advantages of the gases in the mixture. In other words these mixtures when injected as suspensions of microbubbles will provide clear and crisp images with sharp contrasts (typical for microbubbles with good resistance to pressure variations) and at the same time will be resorbed substantially as easily as if filled with air or oxygen only. Thus by combining air, nitrogen, carbon dioxide or oxygen with a certain controlled amount of any of the known biocompatible high molecular weight substances which at the body temperature are gases, ultrasound contrast media with important and totally unexpected advantages are obtained. As explained above, these media provide the best of each components i.e. a good resistance to pressure variations from one and a relatively rapid resorption from the other and at the same time eliminating respective disadvantages of each component taken alone in the media. This is particularly surprising as one would have expected properties averaging those of the components taken separately.

As long as the molecular weight of such biocompatible substances (B) is greater than 80 daltons and their solubility in water is below 0.0283 ml of gas per ml of water under standard conditions, such substances in the gaseous or liquid state are useful for the contrast media of the invention.

Although in conjunction with suitable surfactants and stabilisers, gases like sulfur hexafluoride, tetrafluoromethane, chlorotrifluoromethane, dichlorodifluoro-methane, bromotrifluoromethane, bromochliorodifluoro-methane, dibromo-difluoromethane dichlorotetrafluoroethane, chloropentafluoroethane, hexafluoroethane hexafluoropropylene, octafluoropropane, hexafluoro-butadiene, octafluoro-2-butene, octafluorocyclobutane, decafluorobutane, perfluorocyclopentane, dodecafluoropentane and more preferably sulfur hexafluoride and/or octafluorocyclobutane, may be used in category B, the media of the invention preferably contains as gas B a gas selected from sulfur hexafluoride, tetrafluoromethane, hexafluoroethane, hexafluoro-propylene, octafluoropropane, hexafluorobutadiene, octafluoro-2-butene, octafluorocyclobutane, decafluorobutane, perfluorocyclopentane, dodecafluoropentane and more preferably sulfur hexafluoride and/or octafluorocyclobutane.

Another unexpected and surprising feature of the invention is the fact that when the criteria of WO 93/05819 are applied to the media of the present invention the Q coefficient obtained with the present gas mixtures is below 5. This is astounding since, according to WO 93/05819 media with Q coefficients below 5 are to be excluded from gases suitable for preparing useful ultrasound contrast media. Nevertheless, it has been found that the uniform gas mixtures of the present invention although having a Q coefficient well below 5, still provide contrast agents useful for ultrasound imaging.

When filled with the contrast media of the invention and dispersed in an aqueous carrier containing usual surfactants, additives and stabilisers, the microbubbles formed provide a useful contrast agent for ultrasonic imaging. In addition to the microbubbles, the contrast agent of the invention will contain surfactants additives and stabilizers. Surfactants which may include one or more film forming surfactants in lamellar or laminar form are used to stabilize the microbubble evanescent gas/liquid envelope. Hydrating agents and/or hydrophilic stabilizer compounds such as polyethylene glycol, carbohydrates such as lactose or sucrose, dextran, starch, and other polysaccharides or other conventional additives like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyakylated; mono-, di- and triglycerides of saturated or unsaturated fatty acids; glycerides of soya-oil and sucrose may also be used. Surfactants may be film forming and non-film forming and may include polymerizable amphiphilic compounds of the type of linoleyl-lecithins or polyethylene dodecanoate. Preferably, the surfactants are film forming and more preferably are phospholipids selected from phosphatidic acid, phosphatidyicholine, phosphatidylethanolamine, phosphatidylserine, phosphatidylglycerol phosphatidylinositol, cardiolipin, sphingomyelin and mixtures thereof.

It is understood that the invention is not limited to the contrast agents in which only microbubbles are used as carriers of the ultrasound contrast media of the invention. Any suitable particle filled with the ultrasound contrast medium e.g. liposomes or microballoons having an envelope produced from synthetic or natural polymers or proteins may conveniently be used. Thus it has been established that microballoons prepared with albumin, or liposome vesicles or iodipamide ethyl ester porous particles when filled with the ultrasound contrast media of the invention, provide good echographic contrast agents. Suspensions in which the microbubbles were stabilised with sorbitol or non-ionic surfactants such as polyoxyethylene/polyoxypropylene copolymers (commercially known as Pluronic®) have demonstrated equally good imaging capability when compared to that of the original formulations made with the pure substances taken alone. It is therefore, believed that the invention offers a more generalised concept of ultrasound media and offers better insight into the problems of ultrasound imaging as well as better control of contrast agent properties. The media and contrast agents containg the media of the invention are, therefore, considered as products which take the technique one step further in its development.

The invention also comprises a method of making the ultrasound contrast agent, in which a gas mixture of at least two components is suspended in a physiologically acceptable aqueous carrier liquid containing usual surfactants and stabilisers so as to form gas filled microbubbles or microballoons, characterised in that the minimum effective proportion of at least one gas component (B) in said mixture of gases is determined according to the criteria $$B_c\% = K/e^{b \, M_{wt}} + C$$

in which $B_c\%$ (by vol.) is the total quantity of the component B in the mixture, K & C are constants with values of 140 and −10.8 respectively, $M_{wt}$ represents the molecular weight of the component B exceeding 80 and b is quantity that is a complex function of operating temperature and thickness of the membrane (a lipid film) that stabilizes the microbubbles; however, since the body temperature is substantially constant and the stabilizer film structure substantially independent of lipid concentration, the value of b keeps in the interval 0.011–0.012 and it may be considered as constant. The contrast agents made according to the method comprise suspensions of microbubbles or microballoons with excellent resistance to pressure variations and a relatively rapid resorption. Both of the properties are controlled to the extent that practically custom-tailored echographic agents are now possible. With the above criteria it is possible to produce an agent with desired characteristics starting from any available non-toxic ("of the shelf") substance which at body temperature is gas and which has the molecular weight and solubility in water as explained above.

The invention also includes a dry formulation comprising surfactants, additives and stabilisers stored under a mixture of substances which at the body temperature are gases at least one of which is a gas whose molecular weight is greater than 80 daltons and whose solubility in water is below 0.0283 ml per ml of water under standard conditions. Prior to injection the formulation comprising lyophilised film forming surfactants and optionally, hydrating agents like polyethylene glycol or other conventional hydrophilic substances, is admixed with a physiologically acceptable carrier liquid to produce the ultrasound contrast agent of the invention. The film forming surfactant is, preferably, a phospholipid selected from phosphatidic acid, phosphatidylcholine, phosphatidylethanolamine, phosphatidylserine, phosphatidylglycerol phosphatidylinositol, cardiolipin, sphingomyelin and mixtures thereof.

In a variant, stabilisation of the microbubble evanescent gas/liquid envelope may be secured by non-ionic surfactants such as copolymers of polyoxyethylene and polyoxypropylene in combination with a film forming surfactant such as dipalmitoylphosphatidylglycerol. As before the aqueous liquid carrier may further contain hydrophilic additives such as glycerol, PEG, sorbitol, etc. Furthermore, useful agents of the invention may be prepared with saline solutions containing Tween® 20, sorbitol, soybean oil, and optionally other additives.

Also disclosed is a two-component kit comprising as the first component a dry formulation of surfactants, additives and stabilisers stored under a mixture of gases and as the second component a physiologically acceptable carrier liquid which when brought in contact with the first component provides an ultrasound contrast media. The kit may include a system of two separate vials, each containing one of the components, which are interconnected so that the components may be conveniently brought together prior to use of the contrast agent. Clearly, the vial containing the dry formulation will at the same time contain the ultrasound medium of the invention. Conveniently, the kit may be in the form of a pre-filled two compartment syringe and may further include means for connecting a needle on one of its ends.

The invention further comprises a method of making contrast agents with microbubbles containing the ultrasound contrast media, as well as their use in imaging of organs in human or animal body.

When used for imaging of organs in human or animal body the ultrasound contrast medium of the invention is administered to the patient in the form of an aqueous suspension in the above described physiologically acceptable carrier liquid and the patient is scanned with an ultrasound probe whereby an image of the organ or the part of the body imaged is produced.

The following examples further illustrate the invention:

EXAMPLE 1

Multilamellar vesicles (MLVs) were prepared by dissolving 120 mg of diarachidoylphosphatidylcholine (DAPC, from Avanti Polar Lipids) and 5 mg of dipalmitoylphosphatidic acid (DPPA acid form, from Avanti Polar Lipids) in 25 ml of hexane/ethanol (8/2, v/v) then evaporating the solvents to dryness in a round-bottomed flask using a rotary evaporator. The residual lipid film was dried in a vacuum dessicator and after addition of water (5 ml), the mixture was incubated at 90° C. for 30 minutes under agitation. The resulting solution was extruded at 85° C. through a 0.8 μm polycarbonate filter (Nuclepore®). This preparation was added to 45 ml of a 167 mg/ml solution of dextran 10,000 MW (Fluka) in water. The solution was thoroughly mixed, transferred in a 500 ml round-bottom flask, frozen at −45° C. and lyophilised under 13.33 Nt/m² (0.1 Torr). Complete sublimation of the ice was obtained overnight. Aliquots (100 mg) of the resulting lyophilisate were introduced in 20 ml glass vials. The vials were closed with rubber stoppers and the air removed from vials using vacuum. Mixtures of air with various amounts of sulfur hexafluoride were introduced into the vials via a needle through the stopper.

Bubble suspensions were obtained by injecting in each vial 10 ml of a 3% glycerol solution in water followed by vigorous mixing. The resulting microbubble suspensions were counted using a hemacytometer. The mean bubble size was 2.0 μm. In vitro measurements (as defined in EP-A-0 554 213) of the critical pressure (Pc), echogenicity (i.e. backscatter coefficient) and the bubble count for various samples were performed (see Table 1).

As it may be seen from the results, the microbubbles containing 100% air (sample A) have a low resistance to pressure. However, with only 5% $SF_6$, the resistance to pressure increases considerably (sample B). With 25% $SF_6$

TABLE 1

| Sample | air % vol | $SF_6$ % vol | Q coeff. | Pc mmHg | Echogenicity 1/(cm.sr) × 100 | Concentration (bubbles/ml) |
|---|---|---|---|---|---|---|
| A | 100 | 0 | 1.0 | 43 | 1.6 | $1.5 \times 10^8$ |
| B | 95 | 5 | 1.3 | 68 | 2.1 | $1.4 \times 10^8$ |
| C | 90 | 10 | 1.6 | 85 | 2.4 | $1.5 \times 10^8$ |
| D | 75 | 25 | 3.1 | 101 | 2.3 | $1.4 \times 10^8$ |
| E | 65 | 35 | 4.7 | 106 | 2.4 | $1.5 \times 10^8$ |
| F | 59 | 41 | 5.8 | 108 | 2.4 | $1.6 \times 10^8$ |
| G | 0 | 100 | 722.3 | 115 | 2.3 | $1.5 \times 10^8$ | the resistance to pressure is almost identical to that of 100% $SF_6$. On the other hand, the bubble concentrations, the mean bubble sizes and the backscatter coefficients are almost independent of the percentage of $SF_6$.

Figure 5:
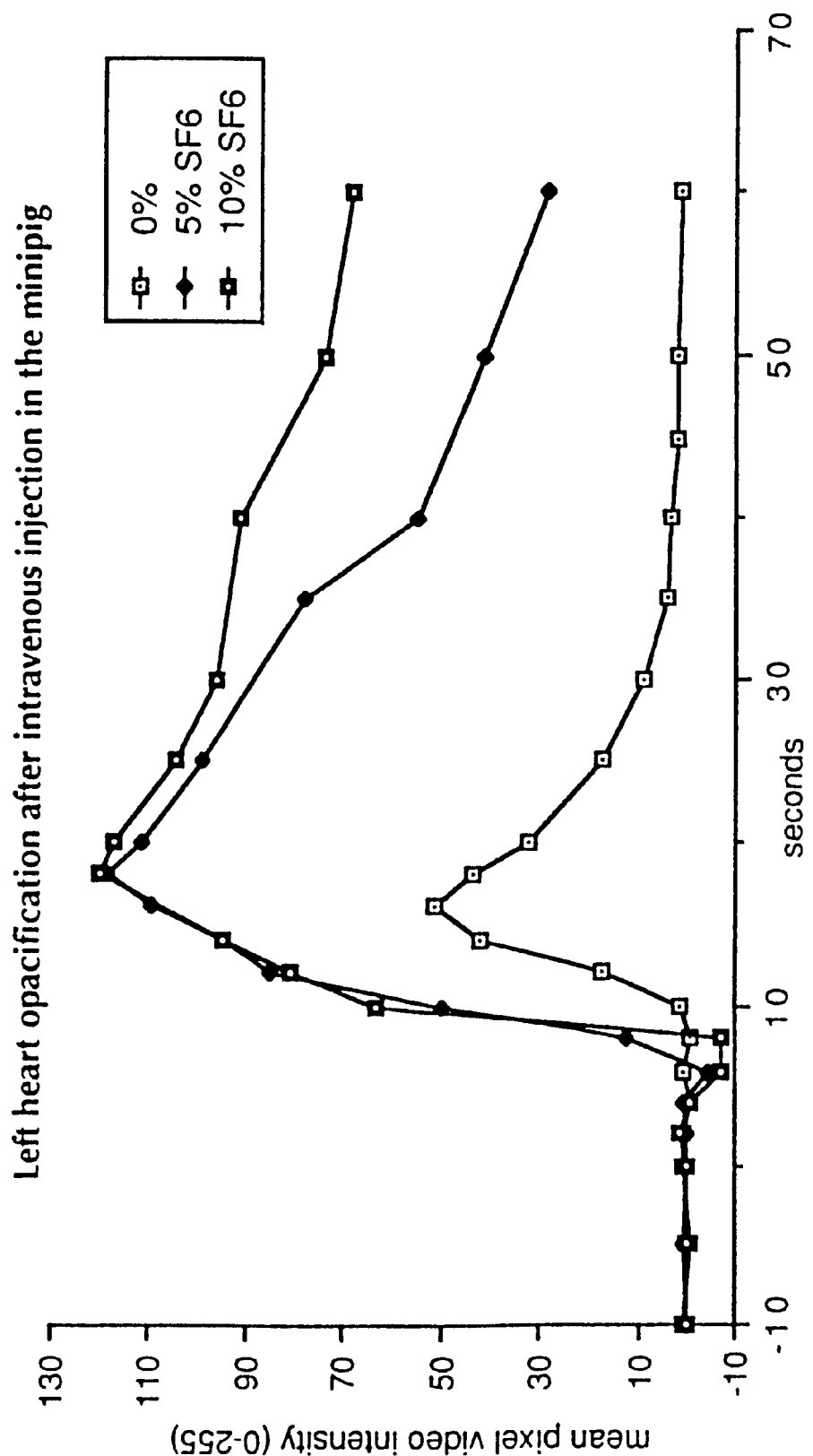
FIG. 5 is a graphic representation of the in vivo echographic responses obtained as a function of time in the left ventricle of a minipig after intravenous injection of contrast media containing various concentrations of $SF_6$.

The resulting suspensions were injected intravenously into minipigs (Pitman Moore) at a dose of 0.5 ml per 10 kg and the images of the left ventricular cavity were recorded on a video recorder. In vivo echographic measurements were performed using an Acuson XP128 ultrasound system (Acuson Corp. USA) and a 7 MHz sector tranducer. The intensity of the contrast was measured by video densitometry using an image analyser (Dextra Inc.). FIG. 5 shows the video densitometric recordings in the left heart of a minipig. Again a considerable difference is observed between the 100% air case (sample A) and the 95% air case (sample B). In particular, with 5% $SF_6$ the maximum intensity is already almost achieved and the half life in circulation shows also a very rapid increase. With 10% $SF_6$, there is no additional increase in intensity but only a prolongation of the half-life. From the example, it follows that using more than 10% to 25% $SF_6$ in the gas mixture provides no real benefit. It is interesting to note that the values of the Q coefficient obtained for the mixtures used were well below the critial value of 5 stipulated by WO-A-93/05819.

EXAMPLE 2

Aliquots (25 mg) of the PEG/DAPC/DPPA lyophilisate obtained as described in Example 1 (using PEC 4000 instead of dextran 10,000) were introduced in 10 ml glass vials. Tedlar® sampling bags were filled with air and octafluorocyclobutane ($C_4F_8$). Known volumes were withdrawn from the bags by syringes and the contents thereof were mixed via a three way stopcock system. Selected gas mixtures were then introduced into the glass vials (previously evacuated). The lyophilisates were then suspended in 2.5 ml saline (0.9% NaCl). The results presented below show the resistance to pressure, the bubble concentration and the backscatter coefficient of the suspensions. In the case of 100% $C_4F_8$ the resistance to pressure reached to 225 mm Hg, (compared to 43 mm Hg in the case of air). Again a considerable increase in pressure resistance was already observed with only 5% $C_4F_8$ (Pc=117 mmHg).

Figure 6:
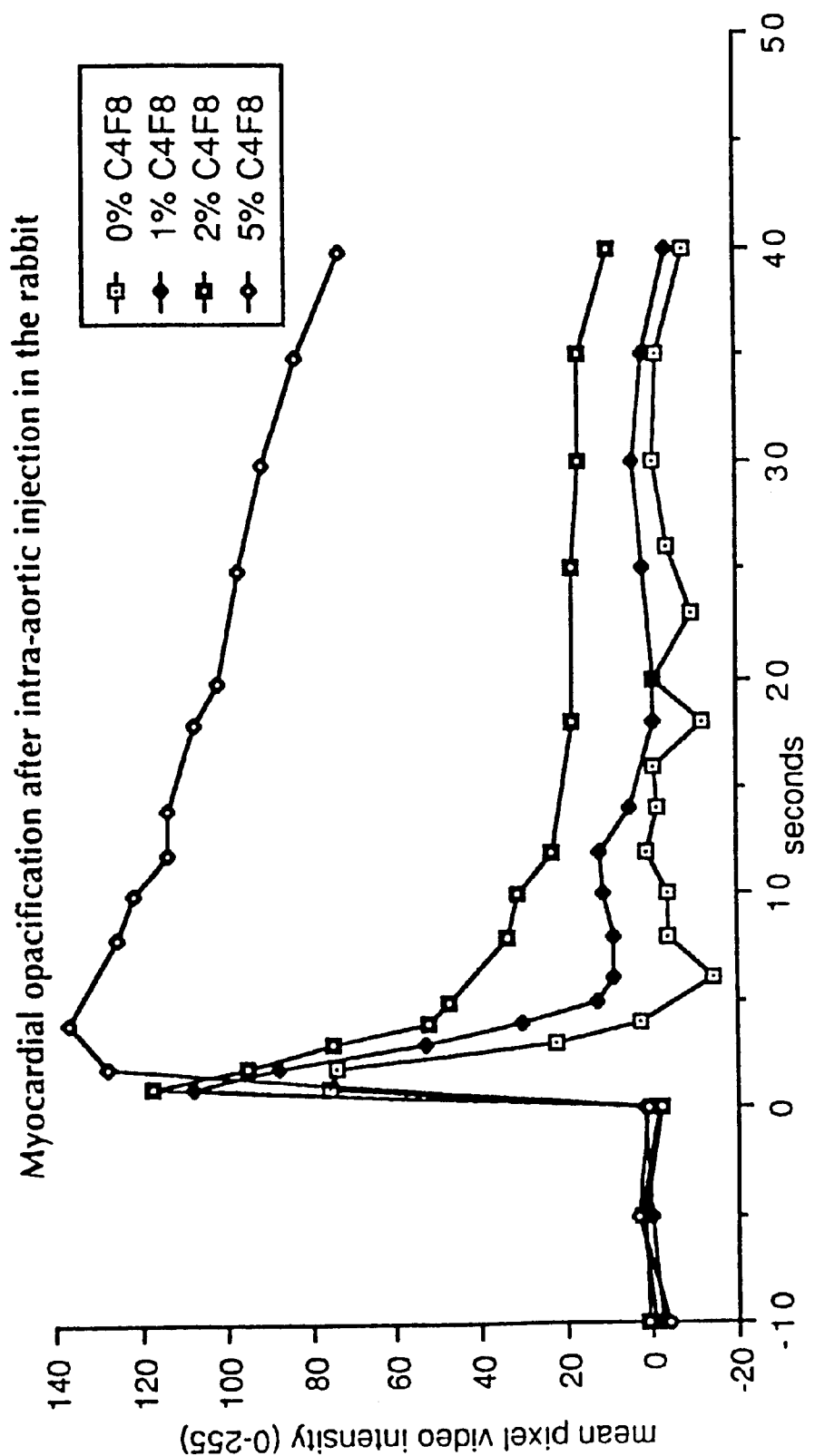
FIG. 6 represents a diagram ofin vizo echographic response obtained as a function of time with contrast media containing various concentrations of $C_4F_8$.

After intra-aortic injection in rabbits (0.03 ml/kg), a slight prolongation of the contrast effect in the myocardium was noticed already with 2% $C_4F_8$ (when compared to air). However with 5% $C_4F_3$, the duration of the contrast increased considerably as if above a threshhold value in the resistance to pressure, the persistence of the bubbles increases tremendously (see FIG. 6).

TABLE 2

| Sample | air % vol | $C_4F_8$ % vol | Q coeff. | Pc mmHg | Echogenicity 1/(cm.sr) × 100 | Concentration (bubbles/ml) |
|---|---|---|---|---|---|---|
| A | 100 | 0 | 1.0 | 43 | 1.6 | $1.8 \times 10^8$ |
| B | 95 | 5 | 1.4 | 117 | 2.2 | $3.1 \times 10^8$ |
| C | 90 | 10 | 1.7 | 152 | 3.1 | $4.7 \times 10^8$ |
| D | 75 | 25 | 3.3 | 197 | 3.5 | $4.9 \times 10^8$ |
| E | 65 | 35 | 4.6 | 209 | 3.4 | $4.3 \times 10^8$ |
| F | 59 | 41 | 5.5 | 218 | 2.8 | $4.0 \times 10^8$ |
| G | 0 | 100 | 1531 | 225 | 2.3 | $3.8 \times 10^8$ |

Here again, this combination of gases provided very good images at 5% of gas B in the mixture, while excellent images of the left heart were obtained with the mixtures containing up to 25% of octafluoro cyclobutane.

Figure 2:
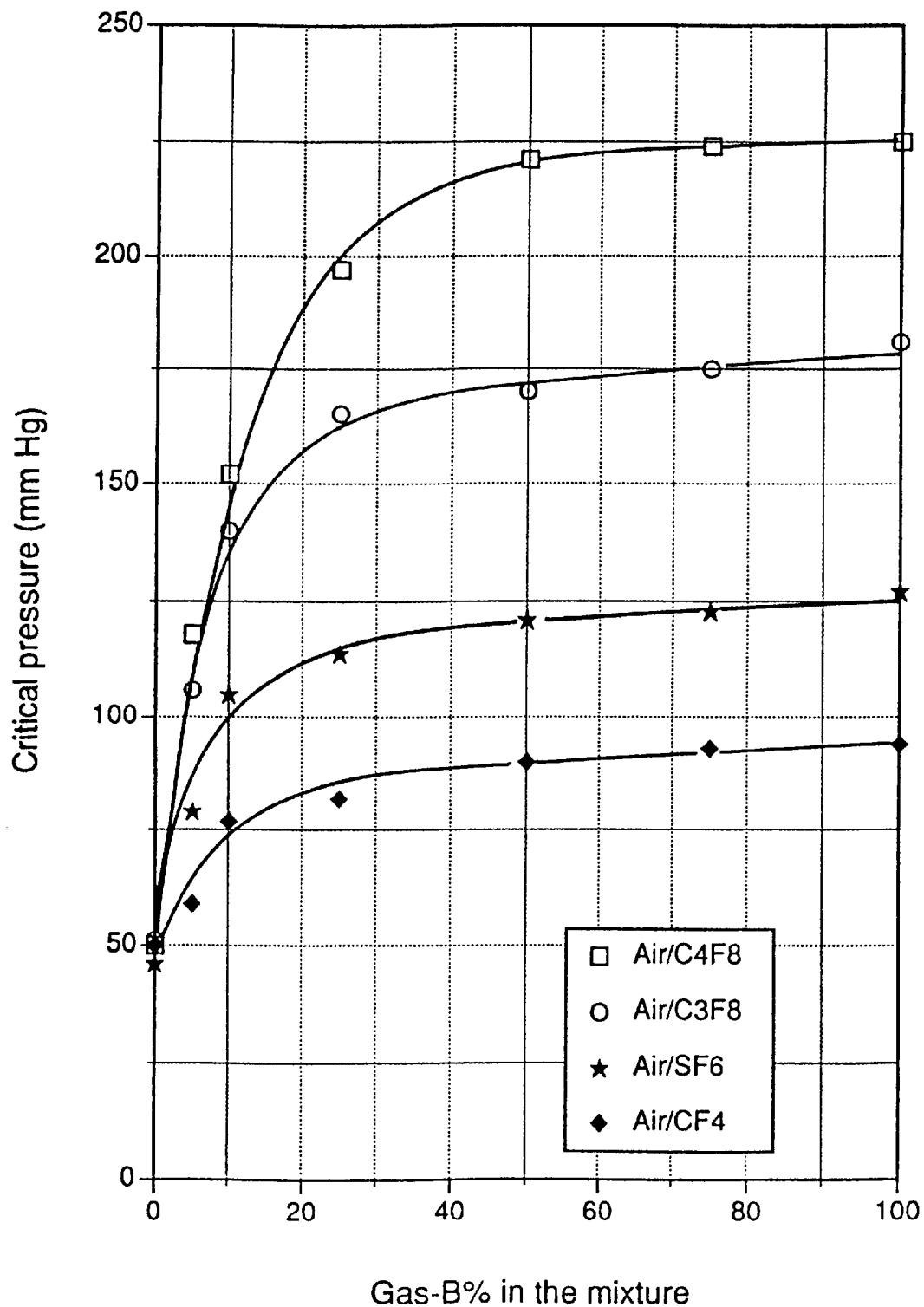
FIG. 2 is schematic diagram of the critical pressure (Pc) of the contrast medium as a function of the quantity of a chosen gas in the mixture.

Corresponding diagram of critical pressure as a function of $C_4F_8$ in the mixture with air is given in FIG. 2. This example again shows that the use of mixture of gases allows to improve considerably the resistance to pressure of air bubbles simply by adding a small percentage of a high molecular weight/low solubility gas. The figure further shows that by appropriate selection of the gas mixture it becomes possible to obtain any desired resistance to pressure.

EXAMPLE 3

The same lyophilisate as that described in Example 5 was used. The gas phase was made of dodecafluoropentane ($C_5F_{12}$) and air. $C_5F_{12}$ is a liquid at room temperature with a boiling point of 29.5° C. 24 ml glass vials each containing 50 mg of the PEG/DSPC/DPPG lyophilisate obtained as described in Example 5 were put under vacuum, closed under vacuum, then heated at 45° C. Small volumes (a few microliters) of $C_5F_{12}$ were injected in the vials still at 45° C. through the stopper. Air was then introduced to restore atmospheric pressure in the vials. After cooling at room temperature, saline

TABLE 3

| Sample | air % vol | $C_5F_{12}$ % vol | Q coeff. | Pc mmHg | Echogen (cm. sr)$^{-1}$ | Conc. (bub/ml) | half-life ($t_{1/2}$) sec | Inten Gray level | AUC ($t_{1/2}$) |
|---|---|---|---|---|---|---|---|---|---|
| A | 100 | 0 | 1.0 | 43 | 0.017 | $1.8 \times 10^8$ | 11 | 22 | 78 |
| B | 99.5 | 0.5 | 1.0 | 80* | — | — | — | — | — |
| C | 98.6 | 1.4 | 1.1 | 133 | 0.026 | $3.9 \times 10^8$ | 14 | 97 | 609 |
| D | 97.1 | 2.9 | 1.4 | 182 | 0.028 | $3.9 \times 10^8$ | 17 | 98 | 860 |
| E | 94.2 | 5.8 | 1.7 | 295 | 0.040 | $5.2 \times 10^8$ | 59 | 99 | 3682 |
| F | 85.5 | 14.5 | 3.4 | 394 | 0.036 | $4.5 \times 10^8$ | 78 | 97 | 5141 |

Figure 3:
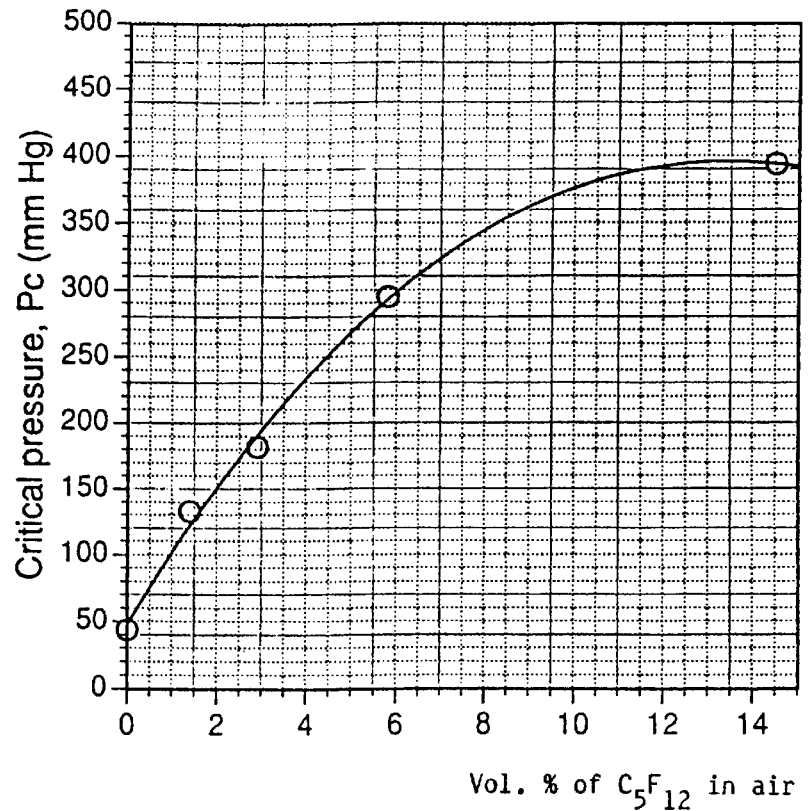
FIG. 3 represents a diagram of the critical pressure (Pc) of a contrast medium made with octafluorocyclobutane ($C_4F_8$) and dodecafluoropentane ($C_5F_{12}$) as a function of quantity of gas in the mixture.
Figure 3:
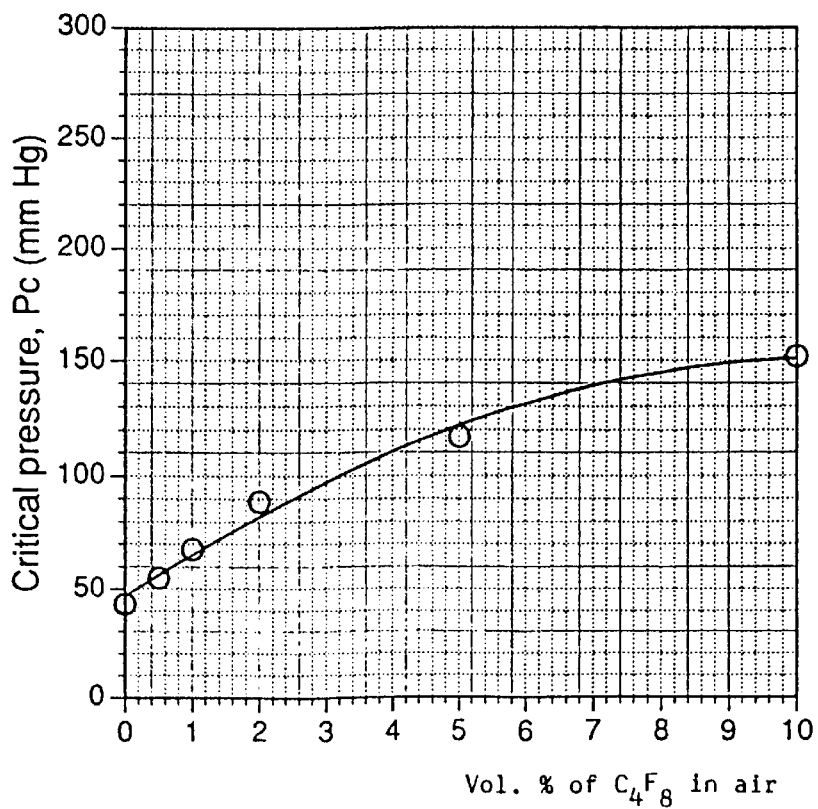
Figure 4:
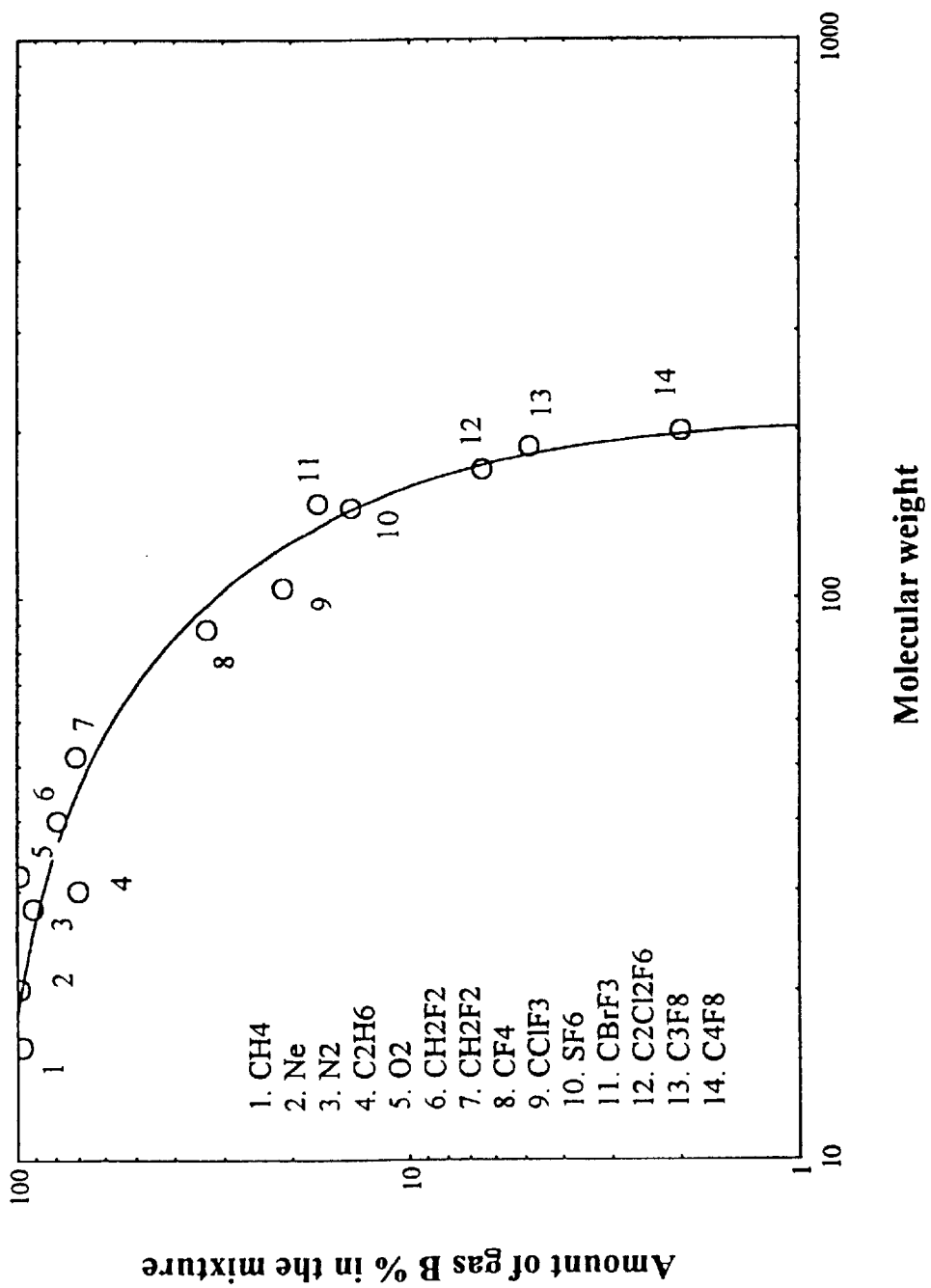
FIG. 4 is a diagram of the minimum amount of a gas in the mixture as a function of the molecular weight.

*Estimated (5 ml) was injected through the stopper and the vials were vigorously agitated. The actual percentage of $C_5F_{12}$ in the gas phase was calculated assuming full vaporization of the liquid introduced. This is an overestimate as at this temperature part of the liquid will not be in gaseous state. As shown in FIG. 3 an increase in the resistance to pressure could already be detected with only 0.5% $C_5F_{12}$ in air. At 1.4% $C_5F_{12}$ the resistance to pressure exceeded 130 mm Hg. These suspensions were also injected intravenously into minipigs (0.5 ml per 15 kg). Intensity was measured by videodensitometry as described in Example 1. As shown in Table 3, maximum intensity was already obtained with 1.4% $C_5F_{12}$. Higher percentages of $C_5F_{12}$ result into prolongation of the half life and increase in the AUC. The half life ($t_{1/2}$) was determined as the time elapsed between injection and the time at which the intensity had dropped to 50% of its maximum value. The area under the curve (AUC) was measured until $t_{1/2}$.

The examples 1–3 also demonstrate that contrary to the statements made in WO-A-93/05819 it is possible to obtain outstanding contrast enhancing agents from gas mixtures whose Q values are smaller and in certain cases much smaller than 5.

EXAMPLE 4

Fifty eight milligrams of diarachidoylphosphatidylcholine (DAPC), 2.4 mg of dipalmitoylphosphatidic acid (DPPA) both from Avanti Polar Lipids (USA) and 3.94 g of polyethyleneglycol (PEG 4000 from Siegfried) were dissolved at 60° C. in tert-butanol (20 ml) in a round-bottom glass vessel. The clear solution was rapidly cooled at −45° C. and lyophilized. Aliquots (25 mg) of the white cake obtained were introduced in 10 ml glass vials.

Tedlar® gas sampling bags were filled with gases, one with air and one with sulfur hexafluoride ($SF_6$). Predetermined volumes of the gases were collected from each bag through the septum by using two separate syringes and the contents mixed via a three way stopcock. The resulting gas mixtures were introduced into 10 ml glass vials which were evacuated and closed with rubber stopper while still under vacuum. Seven vials contained gas mixtures of air and $SF_6$ in different proportions. The concentration of $SF_6$ was between 0 to 100%. The actual percentage of $SF_6$ in the gas phase was confirmed by densimetry (A. Paar densimeter). Saline (0.9% NaCl) was then injected through the stopper into each vial (5 ml per vial) and the powder dissolved by vigorous shaking. The resulting microbubble suspensions were evaluated in vitro and in vivo. The resistance to pressure $P_c$ was determined using a nephelometric assay and the backscatter coefficient was measured using a pulse echo set up (both described in EP-A-0 554 213). The bubble concentration and mean bubble size were determined by analysis with a Coulter Multisizer II (Coulter Electronics Ltd). The results obtained were virtually the same to those given for Example 1.

EXAMPLE 6

The method of the invention was applied to a microbubble suspension prepared as described in Example 1 of WO 92/11873. Three grams of Pluronic® F68 (a copolymer of polyoxyethylene-polyoxypropylene with a

TABLE 5

| air % vol | $C_4F_8$ % vol | Pc (mmHg) | right ventr. opacif. | | | left ventr. opacif. | | |
|---|---|---|---|---|---|---|---|---|
| | | | $t_{1/2}$ | intens | AUC | $t_{1/2}$ | intens | AUC |
| 100 | 0 | 54 | 4 | 96 | 280 | 9 | 101 | 514 |
| 99 | 1 | 89 | 7 | 98 | 377 | 12 | 98 | 632 |
| 95 | 5 | 136 | 14 | 94 | 829 | 40 | 101 | 2693 |
| air | $C_5F_{12}$ | | | | | | | |
| 95 | 5 | 177 | * | * | * | 43 | 111 | 3249 |

*Shadowing

TABLE 4

| Gas A | Gas B | Gas B % vol | Pc mmHg | Gas A $M_{wt}$ | Gas B $M_{wt}$ | Solubility* Gas A | Solubility* Gas B |
|---|---|---|---|---|---|---|---|
| $O_2$ | $C_4F_8$ | 0 | 40 | 32 | 200 | 0.083 | 0.016 |
| | $C_4F_8$ | 5 | 112 | | | | |
| | $C_4F_8$ | 10 | 148 | | | | |
| $CO_2$ | $C_4F_8$ | 0 | 50 | 44 | 200 | 0.74 | 0.016 |
| | $C_4F_8$ | 5 | — | | | | |
| | $C_4F_8$ | 10 | 204 | | | | |
| $CHClF_2$ | $C_4F_8$ | 0 | — | 86.5 | 200 | 0.78 | 0.016 |
| | $C_4F_8$ | 5 | 106 | | | | |
| | $C_4F_8$ | 10 | 163 | | | | |
| Xenon | $C_4F_8$ | 0 | 50 | 131 | 200 | 0.108 | 0.016 |
| | $C_4F_8$ | 5 | 147 | | | | |
| | $C_4F_8$ | 10 | 181 | | | | |
| $SF_6$ | $C_4F_8$ | 0 | 124 | 146 | 200 | 0.005 | 0.016 |
| | $C_4F_8$ | 5 | 159 | | | | |
| | $C_4F_8$ | 10 | 193 | | | | |
| $N_2$ | $SF_6$ | 0 | 55 | 28 | 146 | 0.0144 | 0.005 |
| | $SF_6$ | 5 | 80 | | | | |
| | $SF_6$ | 10 | 108 | | | | |
| $CF_4$ | $SF_6$ | 0 | 84 | 182 | 146 | 0.0038 | 0.005 |
| | $SF_6$ | 5 | 91 | | | | |
| | $SF_6$ | 10 | 106 | | | | |
| Xenon | $SF_6$ | 0 | 50 | 131 | 146 | 0.108 | 0.005 |
| | $SF_6$ | 5 | 67 | | | | |
| | $SF_6$ | 10 | 83 | | | | |

*Bunsen coefficient

EXAMPLE 5

A PEG/DSPC/DPPG lyophilisate was prepared as described in Example 4 using 30 mg of distearoylphosphatidylcholine (DSPC) and 30 mg dipalmitoylphosphatidylglycerol (DPPG) (both from SYGENA, Switzerland). Aliquots (25 mg) of the resulting cake were introduced in 10 ml glass vials. Different gas mixtures were introduced in various vials by withdrawing appropriate volumes from Tedlar® bags filled with the various gases. Table 4 shows the gas mixtures investigated, their molecular weight and their solubities (expressed as Bunsen coefficient) and the resistance to pressure of the microbubbles obtained. It is particularity interesting to note that highly soluble gases such as $CO_2$, xenon, $CHClF_2$ which alone are very poor in their ability to form stable and resistant bubbles are nevertheless able to give rise to highly stable bubbles provided a small percentage of a gas such as $SF_6$ or $C_4F_8$ is added.

molecular weight of 8400), 1 g of dipalmitoylphosphatidylglycerol and 3.6 g of glycerol were added to 80 ml of distilled water. After heating at about 80° C. a clear homogenous solution was obtained. The tenside solution was cooled to room temperature and the volume adjusted to 100 ml. The bubble suspension was obtained by using two syringes connected via a three-way valve. One of the syringes was filled with 5 ml of the tenside solution while the other was filled with 0.5 ml of air or air/$C_4F_8$ mixture (see Table 5). The three way valve was filled with the tenside solution before it was connected to the gas-containing syringe. By alternatively operating the two pistons, the tenside solution was transferred back and forth between the two syringes (5 times in each direction) and milky suspensions were obtained. After dilution (1/50) in distilled water saturated with air the resistance to pressure (Pc) was determined. Aliquots were injected intravenously into anaesthetized rabbits (0.03 ml/kg) and echographic images of the left ventricle were recorded. The area under the curve (AUC) as well as the half life ($t_{1/2}$) were determined. A considerable increase of the half-life and AUC was observed when using 5% $C_4F_8$ (compared to air). Similar results were obtained with 5% $C_5F_{12}$.

EXAMPLE 7

A suspension of microbubbles was obtained as described in WO-A-93/05819 using mixtures of air and octafluorocyclobutane $C_4F_8$. An aqueous solution containing sorbitol (20 g), NaCl (0.9 g), soybean oil (6 ml), Tween 20

TABLE 6

| air % vol | $C_4F_8$ % vol | right ventr. opacif. | left ventr. opacif. | air % vol | $C_5F_{12}$ % vol | right ventr. opacif. | left ventr. opacif. |
|---|---|---|---|---|---|---|---|
| 100 | 0 | + | − | 100 | 0 | + | − |
| 99 | 1 | + | − | 99 | + | + | + |
| 95 | 5 | ++ | − | 95 | 5 | ++ | ++ |

"−" no opacification
"+" moderate opacification
"++" good opacification (0.5 ml) was prepared and adjusted to 100 ml of distilled water. 10 ml of this solution was taken up in a 10 ml syringe. A second 10 ml syringe was filled with mixtures of air and $C_4F_8$. The two syringes were connected via a three way stopcock. By operating alternatively each of the two pistons for a total of times, milky suspensions were obtained. These suspensions were tested for their resistance to pressure. Aliquots were also injected intravenously into anaesthethized rabbits (0.1 ml/kg) and echographic images of the left ventricle were recorded. Interestingly no contrast was detected in the left ventricle with 1% or even 5% $C_4F_8$. However, left ventricle opacification was obtained with 1% and even more with 5% of $C_5F_{12}$.

EXAMPLE 8

A PEG/DSPC/DPPG lyophilisate was prepared as described in Example 4 using 30 mg of distearoylphosphatidylcholine (DSPC) and 30 mg dipalmitoylphosphatidylglycerol (DPPG) (both from SYGENA, Switzerland). Aliquots (25 mg) of the resulting cake were introduced in 10 ml glass vials. Different gas mixtures were introduced in various vials by withdrawing appropriate volumes from Tedlar® bags filled with the various gases. Table 7 shows the gas mixtures investigated and the resistance to pressure of the microbubbles obtained. It is noteworthy the high molecular weight gas may even be a mixture of two or more gases with high molecular weight and

TABLE 7

| Sample | $C_4F_8$ % vol | $CF_4$ % vol | air % vol | Pc mmHg | Absorbance |
|---|---|---|---|---|---|
| $A_1$ | 5 | 15 | 80 | 113 | 0.284 |
| $A_2$ | 10 | 10 | 80 | 147 | 0.281 |
| $A_3$ | 15 | 5 | 80 | 167 | 0.281 | solubility (expressed as Bunsen coefficient) which is below 0.0283. It follows that in place of a single gas (B), mixtures of two or more activating or minor component gases may also be used. Although, in this example, the critical pressure is proportional to the percentage of the heavier of the two components, it is believed that other combinations of gases may further lower the total amount of the insoluble gas(es) in the mixture through synergy.

What is claimed is:

1. An injectable ultrasound contrast agent comprising a suspension of gas filled microbubbles in a physiologically acceptable aqueous carrier containing usual surfactants, additives and stabilizers, the microbubbles being bounded by a monolayer of saturated phospholipids in laminar or lamellar form, the microbubbles being filled with a gas mixture of at least two biocompatible gases A and B in which at least one gas (B) present in an amount of between 0.5–41% by volume has a molecular weight greater than 80 daltons and solubility in water below 0.0283 ml per ml of water at standard conditions, the balance of the mixture being gas A, wherein gases A and B are both gaseous at body temperature.

2. The ultrasound contrast agent of claim 1 wherein gas (B) is a fluorine-containing biocompatible gas.

3. The ultrasound contrast agent of claim 2 wherein the fluorine-containing gas is $SF_6$.

4. The ultrasound contrast agent of claim 2 wherein the fluorine-containing biocompatible gas contains 1 to 5 carbon atoms.

5. The ultrasound contrast agent of claim 2, wherein the fluorine-containing gas is $CF_4$.

6. The ultrasound contrast agent of claim 2, wherein the fluorine-containing gas is $C_2F_6$.

7. The ultrasound contrast agent of claim 2, wherein the fluorine-containing gas is $C_3F_6$.

8. The ultrasound contrast agent of claim 2, wherein the fluorine-containing gas is $C_3F_8$.

9. The ultrasound contrast agent of claim 2, wherein the fluorine-containing gas is $C_4F_6$.

10. The ultrasound contrast agent of claim 2, wherein the fluorine-containing gas is $C_4F_8$.

11. The ultrasound contrast agent of claim 2, wherein the fluorine-containing gas is $C_4F_8$.

12. The ultrasound contrast agent of claim 2, wherein the fluorine-containing gas is $C_5F_{10}$.

13. The ultrasound contrast agent of claim 2, wherein the fluorine-containing gas is $C_5F_{12}$.

14. The ultrasound contrast agent of claim 3, wherein gas A is air.

15. The ultrasound contrast agent of claim 1, 2 or 4, wherein gas A is oxygen.

16. The ultrasound contrast agent of claim 1, 2 or 4, wherein gas A is nitrogen.

17. The ultrasound contrast agent of claim 1, 2 or 4, wherein gas A is carbon dioxide.

18. The ultrasound contrast agent of claim 1, wherein the aqueous carrier further contains hydrophilic stabilizers.

19. The ultrasound contrast agent of claim 1, wherein the saturated phospholipid is selected from the group consisting of phosphatidic acid, phosphatidylcholine, phosphatidylethanolamine, phosphatidylserine, phosphatidylglycerol, phosphatidyl linositol, cardiolipin, sphingomyelin and mixtures thereof.

20. The ultrasound contrast agent of claim 1, wherein in addition to the phospholipid the aqueous carrier comprises copolymers of polyoxyethylene and polyoxypropylene, and glycerol.

21. The ultrasound contrast agent of claim 1, wherein the surfactants are soy bean oil, Tween and/or sorbitol.

22. The ultrasound contrast agent of claim 3, wherein $SF_6$ is present in an amount of 25–41% by volume the balance being air.

23. The ultrasound contrast agent of claim 10, wherein $C_4F_8$ is present in an amount of 10–41% by volume the balance being air.

24. The ultrasound contrast agent of claim 10, wherein $C_4F_8$ is present in an amount of 15% by volume the balance being air.

25. The ultrasound contrast agent of claim 13, wherein $C_5F_{12}$ is present in an amount of 2.9–4.5% by volume the balance being air.

26. The ultrasound contrast agent of claim 1, wherein the fluorine-containing gas is a mixture of two or more fluorine containing gases.

27. The ultrasound contrast agent of claim 26, wherein the mixture contains $C_4F_8$.

28. The ultrasound contrast agent of claim 26, wherein the mixture contains $CF_4$.

29. The ultrasound contrast agent of claim 26, wherein the mixture consists of 5–15% volume of $C_4F_8$, 80% volume of air, the balance being $CF_4$.

* * * * *